US009795976B2

(12) United States Patent
Eames et al.

(10) Patent No.: US 9,795,976 B2
(45) Date of Patent: Oct. 24, 2017

(54) THERMAL FOGGER FOR CREATING STABLE AEROSOLS

(71) Applicant: 1,4 Group, Inc., Meridian, ID (US)

(72) Inventors: Curtis Lee Eames, Meridian, ID (US); John Bergman, Fargo, ND (US)

(73) Assignee: 1,4Group, Inc., Meridian, ID (US)

( * ) Notice: Subject to any disclaimer, the term of this patent is extended or adjusted under 35 U.S.C. 154(b) by 516 days.

(21) Appl. No.: 14/148,498

(22) Filed: Jan. 6, 2014

(65) Prior Publication Data
US 2014/0191057 A1 Jul. 10, 2014

Related U.S. Application Data

(60) Provisional application No. 61/749,651, filed on Jan. 7, 2013.

(51) Int. Cl.
*B05B 7/16* (2006.01)
*B01F 5/04* (2006.01)
(Continued)

(52) U.S. Cl.
CPC .......... *B05B 7/1626* (2013.01); *B01F 5/0451* (2013.01); *B01F 5/0615* (2013.01); *F41H 9/08* (2013.01); *A01M 13/00* (2013.01); *A01N 25/06* (2013.01); *A01N 47/20* (2013.01); *A23B 7/144* (2013.01); *A23B 7/155* (2013.01); *A23B 7/158* (2013.01); *A23B 7/16* (2013.01); *B01F 5/0614* (2013.01); *B01F 2005/0034* (2013.01); *B01F 2005/0637* (2013.01); *B05B 1/24* (2013.01); *B05B 7/0012* (2013.01); *B05D 1/02* (2013.01)

(58) Field of Classification Search
CPC ... B05B 7/2437; B05B 7/1626; B05B 7/1613; B05B 7/162; B01F 5/0615; B01F 5/0614; A23B 7/14; A23B 7/00; A23B 7/153; A23B 7/152; A23B 7/154; A01N 25/06
See application file for complete search history.

(56) References Cited

U.S. PATENT DOCUMENTS 391,865 A * 10/1888 Schutte ................... F23D 11/10
236/1 R
2,029,141 A * 1/1936 Warner ..................... B05B 7/10
15/322

(Continued)

FOREIGN PATENT DOCUMENTS

CN 201454744 U 5/2010
JP EP 0077130 A1 * 4/1983 ............ B01F 5/0614

OTHER PUBLICATIONS

Mitrovic "Heat Exchangers: Basic design applications" Chapter 12 Helically Coiled Heat Exchangers published Mar. 9, 2012.*
(Continued)

*Primary Examiner* — Amber R Orlando
*Assistant Examiner* — Stephen Hobson
(74) *Attorney, Agent, or Firm* — Magleby Cataxinos & Greenwood

(57) ABSTRACT

An improved thermal fogging device includes an extended heat transfer surface located within the aerosolization chamber that increases the mixing of the liquid chemical particles and the hot gases in the aerosol to improve aerosolization. The extended heat transfer surface also helps to increase the heat transfer to the forming aerosol in the aerosolization chamber.

14 Claims, 12 Drawing Sheets

(51) Int. Cl.
F41H 9/08       (2006.01)
B05D 1/02       (2006.01)
A01N 47/20      (2006.01)
A23B 7/144      (2006.01)
A23B 7/155      (2006.01)
A23B 7/158      (2006.01)
A23B 7/16       (2006.01)
B01F 5/06       (2006.01)
A01N 25/06      (2006.01)
B05B 7/00       (2006.01)
A01M 13/00      (2006.01)
B05B 1/24       (2006.01)
B01F 5/00       (2006.01)

(56) References Cited

U.S. PATENT DOCUMENTS

| | | | | |
|---|---|---|---|---|
| 2,284,255 A | * | 5/1942 | Baureschmidt | E21B 43/12 366/160.1 |
| 2,646,854 A | * | 7/1953 | Walker | F01N 1/085 181/280 |
| 2,662,332 A | * | 12/1953 | McIntire | A01M 1/2077 392/379 |
| 2,685,146 A | * | 8/1954 | Stevens | A01M 13/00 239/129 |
| 2,789,893 A | * | 4/1957 | Coats | B01F 3/04007 48/190 |
| 2,901,182 A | * | 8/1959 | Cragg | A01M 7/0003 239/129 |
| 3,069,092 A | * | 12/1962 | Norvell, Jr. | A01M 1/2077 239/133 |
| 3,128,170 A | | 4/1964 | Plant | |
| 3,134,191 A | * | 5/1964 | Davis | A01M 13/00 222/146.1 |
| 3,239,960 A | * | 3/1966 | Stevens | A01M 13/00 239/135 |
| 3,326,538 A | * | 6/1967 | Merritt | F02M 19/03 239/142 |
| 3,458,948 A | * | 8/1969 | Schlensker | A01M 13/00 219/530 |
| 3,496,668 A | * | 2/1970 | Slater | B05B 7/1686 392/397 |
| 3,548,532 A | * | 12/1970 | Landwer | A01M 1/2088 43/129 |
| 3,595,481 A | * | 7/1971 | Enblom | A01M 13/00 239/129 |
| 3,949,970 A | * | 4/1976 | ter Braak | B01F 5/0614 239/432 |
| 3,986,670 A | * | 10/1976 | Syveson | A01M 13/00 239/133 |
| 4,133,485 A | * | 1/1979 | Bouvin | B01F 5/0614 138/42 |
| 4,155,249 A | * | 5/1979 | Scott | G01M 3/20 239/129 |
| 4,226,179 A | | 10/1980 | Sheldon, III et al. | |
| 4,270,576 A | * | 6/1981 | Takeda | B01F 5/0451 137/888 |
| 4,409,002 A | * | 10/1983 | Zwicker | B01F 5/0614 239/424.5 |
| 4,512,515 A | * | 4/1985 | Tenney | A01G 13/06 239/129 |
| 4,527,712 A | * | 7/1985 | Cobbs, Jr. | B05B 7/168 222/1 |
| 4,595,142 A | * | 6/1986 | Kawaharazuka | A01M 7/0021 239/373 |
| 4,675,504 A | * | 6/1987 | Suhajda | A01M 1/2077 239/136 |
| 4,703,155 A | | 10/1987 | Suhajda | |
| 4,735,134 A | | 4/1988 | Brouwer | |
| 4,811,901 A | | 3/1989 | Stevens et al. | |
| 4,887,525 A | | 12/1989 | Morgan | |
| 4,977,825 A | | 12/1990 | Morgan | |
| 5,009,152 A | | 4/1991 | Morgan | |
| 5,222,666 A | * | 6/1993 | Gnutel | A01M 7/006 222/146.3 |
| 5,240,183 A | | 8/1993 | Bedaw et al. | |
| 5,423,488 A | * | 6/1995 | Filion | B29B 7/32 239/488 |
| 5,605,400 A | * | 2/1997 | Kojima | B01F 5/061 366/339 |
| 5,723,184 A | * | 3/1998 | Yamamoto | A01M 17/008 118/300 |
| 5,935,660 A | * | 8/1999 | Forsythe | A01N 25/06 239/290 |
| 6,027,241 A | * | 2/2000 | King | B01F 3/0873 138/38 |
| 6,053,435 A | * | 4/2000 | Hung | A63J 5/025 239/136 |
| 6,068,888 A | | 5/2000 | Forsythe et al. | |
| 6,102,561 A | * | 8/2000 | King | B01F 5/0614 138/38 |
| 6,322,002 B1 | * | 11/2001 | Forsythe | B05B 7/164 239/135 |
| 6,432,882 B1 | * | 8/2002 | Yamamoto | A01N 47/20 504/116.1 |
| 6,723,364 B1 | | 4/2004 | Bompeix et al. | |
| 6,855,669 B2 | | 2/2005 | Knowles et al. | |
| 8,178,145 B1 | | 5/2012 | Micka et al. | |
| 8,241,410 B1 | * | 8/2012 | Pease | B01D 47/10 261/DIG. 54 |
| 8,672,235 B2 | * | 3/2014 | Sardo | A23B 7/153 137/113 |
| 8,696,193 B2 | * | 4/2014 | Herbstritt | B01F 3/12 366/338 |
| 2002/0110714 A1 | * | 8/2002 | Andrews | B01D 1/0017 429/413 |
| 2005/0288184 A1 | * | 12/2005 | Keim | A01N 25/00 504/116.1 |
| 2006/0120214 A1 | * | 6/2006 | Raftis | B01F 5/0614 366/165.2 |
| 2007/0290062 A1 | * | 12/2007 | Forsythe | A23B 7/152 239/8 |
| 2009/0019843 A1 | * | 1/2009 | Levin | B01F 3/04049 60/303 |
| 2009/0062126 A1 | | 3/2009 | Knowles et al. | |
| 2010/0107614 A1 | * | 5/2010 | Levin | B01F 3/04049 60/303 |
| 2010/0230516 A1 | * | 9/2010 | Solie | B01F 5/0614 239/428 |
| 2011/0044852 A1 | * | 2/2011 | Ryan | A01M 13/00 422/32 |
| 2011/0142429 A1 | * | 6/2011 | Joseph | A63J 5/025 392/394 |
| 2012/0111961 A1 | * | 5/2012 | Arnold | A01M 7/0014 239/1 |
| 2012/0266521 A1 | * | 10/2012 | Asciutto | A01M 17/004 43/127 |
| 2013/0037974 A1 | * | 2/2013 | Nishikawa | B01F 5/0451 261/152 |
| 2013/0180595 A1 | * | 7/2013 | Naunheimer | B01J 8/0492 137/13 |
| 2013/0239546 A1 | * | 9/2013 | Levin | B01F 5/0268 60/274 |
| 2015/0043304 A1 | * | 2/2015 | Franks | A01M 13/00 366/167.1 |
| 2016/0032809 A1 | * | 2/2016 | Kobe | B01F 5/0614 60/324 |

OTHER PUBLICATIONS

"Convective heat transfer" The Engineering ToolBox at <http://web.archive.org/web/20120106134320/http://www.engineeringtoolbox.com/convective-heat-transfer-d_430.html> published online Jan. 6, 2012.*

International Search Report for International Application No. PCT/US2014/010372, dated Aug. 8, 2014.

(56) References Cited

OTHER PUBLICATIONS

Written Opinion of the International Searching Authority for International Application No. PCT/US2014/010372, (dated Jul. 18, 2014), 5 pages.
Supplementary Partial European Search Report for European Application No. 14735250.4, (dated Aug. 11, 2016), 4 pages.
Extended European Search Report for European Application No. 14735250.4, (dated Nov. 24, 2016), 11 pages.
"Curtis Dyna-Fog, Ltd. Innovators of Spraying & Fogging Technology Since 1947," Curtis Dyna-Fog Ltd., http://www.dynafog.com/foggers/index.htm, (accessed Sep. 25, 2012), 3 pages.
"Foggers," http://www.aloginc.net/Alog_Company_Inc/Foggers/foggers.html, (accessed Sep. 25, 2012), 4 pages.

* cited by examiner

THERMAL FOGGER FOR CREATING STABLE AEROSOLS

CROSS-REFERENCE TO RELATED APPLICATION

This application claims the benefit of U.S. Provisional Patent Application Ser. No. 61/749,651, filed Jan. 7, 2013, the disclosure of which is hereby incorporated herein in its entirety by this reference.

FIELD

This disclosure relates generally to devices for forming aerosols and to thermal fogging devices.

BACKGROUND

Aerosols of various types of chemicals have been used for numerous agricultural purposes, such as mosquito abatement, weed control and treatment of post-harvest crops. Examples of various types of thermal foggers used to create aerosols are identified in the following U.S. Patents: U.S. Pat. Nos. 5,935,660, 6,322,002, and 6,068,888 to Forsythe et al., U.S. Pat. No. 6,723,364 to Bompiex et al., as well as in product literature from Curtis Dyna-Fog, Ltd.

Such thermal foggers generally operate by mixing a flowing stream of hot gas with a measured amount of a liquid chemical to be aerosolized. The hot gas stream may be combustion gases, as in the U.S. Pat. No. 6,322,002 ('002 Patent) to Forsythe et al., or a hot air stream, as in the U.S. Pat. No. 6,723,364 ('364 Patent) to Bompiex et al. Regardless of the type of hot gas utilized, the efficiency and capacity of such a fogger and the quality of the fog (aerosol) produced depends upon the interaction of the hot gas and the liquid chemical in an aerosolization chamber of the fogger. For certain purposes, such as mosquito abatement and weed control, the efficiency of the fogger and the quality of the aerosol may be of minor importance. However, for other purposes, such as the fogging of chemicals to treat stored crops and treatment of stored potatoes with sprout inhibitors, the capacity, efficiency and quality of the aerosol are of prime importance. Certain techniques involved in treating potato storage facilities are indicated in U.S. Pat. No. 4,887,525 to Morgan.

In many treatment applications, the quality and uniformity of the aerosol is important. For example, for the aerosolization of molten CIPC (isopropyl-N-chlorophenyl-carbamate), a stable, persistent aerosol is important to achieve efficient thermal fogging.

Methods of application and structural improvements are ongoing in crop-storage facilities, such as in the potato storage industry, particularly to improve the capacity, efficiency and/or quality of thermal foggers and the aerosols produced therefrom.

SUMMARY

The unique thermal foggers of the instant invention improve the quality of aerosols produced within such thermal foggers in an energy-efficient manner. The extended, disruptive flow-surface element can be placed in a fixed position within the aerosolization chamber of a thermal fogger to cause a circuitous flow, wherein the entrained liquid particles of the aerosol contact the hot extended surface more frequently, thereby improving heat transfer from the hot extended surface to the liquid particles to create an improved stable aerosol.

In a particular embodiment, a thermal fogger having an improved construction and operation is disclosed. The thermal fogger includes a heating chamber to heat a hot gas to a predetermined temperature. The heating chamber is in communication with an aerosolization chamber to which the hot gas and a liquid chemical stream are introduced. An extended-surface element structured and adapted to be inserted into the aerosolization chamber increases turbulent flow and heat transfer to the forming aerosol. The extended-surface element may include an auger or screw-shaped element. The extended-surface element may be in a fixed, but removable position within the aerosolization chamber.

In another embodiment, a thermal fogger having improved aerosolization means is disclosed. The thermal fogger includes a heating chamber to heat a gas to a predetermined temperature. The thermal fogger may also include an aerosolization chamber with a mixing means that causes the hot gas and a liquid chemical stream, which may also be pre-heated, to travel a convoluted path and contact an extended-surface of the mixing means as the respective streams mix and travel through the aerosolization chamber.

In yet another embodiment, a thermal fogger with a heating chamber and an aerosolization chamber is disclosed. The aerosolization chamber includes an extended-surface element adapted and configured to fit within the aerosolization chamber. The outer dimension of the extended-surface element may be substantially similar to the inside diameter of the aerosolization chamber. The extended-surface element has a convoluted surface that interrupts and diverts the flow of the forming aerosol particles causing the forming aerosol to travel a circuitous path through the aerosolization chamber rather than travelling substantially linearly through the aerosolization chamber.

A further embodiment includes a retrofit device for insertion into an existing thermal fogger wherein the retrofit device has an extended-surface area structure that increases heat transfer and turbulence in the aerosolization chamber of a thermal fogger. The retrofit device may be adapted and configured to have an outer diameter that is substantially the same as the inner diameter of the barrel of the aerosolization chamber of the existing thermal fogger.

A particular embodiment includes a heat exchange surface element for a tubular-shaped thermal fogger aerosolization chamber that may be configured as a screw conveyor-type element with spiral-shaped flights. Such an element may be in a fixed position within the aerosolization chamber of the thermal fogger. The flights can have a substantially uniform maximum diameter that is substantially the same as the inside diameter of the tubular-shaped thermal fogger aerosolization chamber. In some embodiments, the spiral-shaped element may be fixed within a tube or pipe wherein the inner diameter of the tube and the outer diameter of the spiral-shaped element are matched with one another and the outer diameter of the tube is only slightly smaller than the inner diameter of the barrel of thermal fogger into which the tube or pipe can be inserted and secured. The tube into which the spiral-shaped element is fixed may be a ceramic tube or another type of heat resistant or electrically insulated tube.

BRIEF DESCRIPTION OF THE DRAWINGS

While the specification concludes with claims particularly pointing out and distinctly claiming what are regarded as embodiments of the disclosure, various features and advantages of this disclosure may be more readily ascertained from the following description of example embodiments provided with reference to the accompanying drawings, in which:

DETAILED DESCRIPTION

Figure 1:
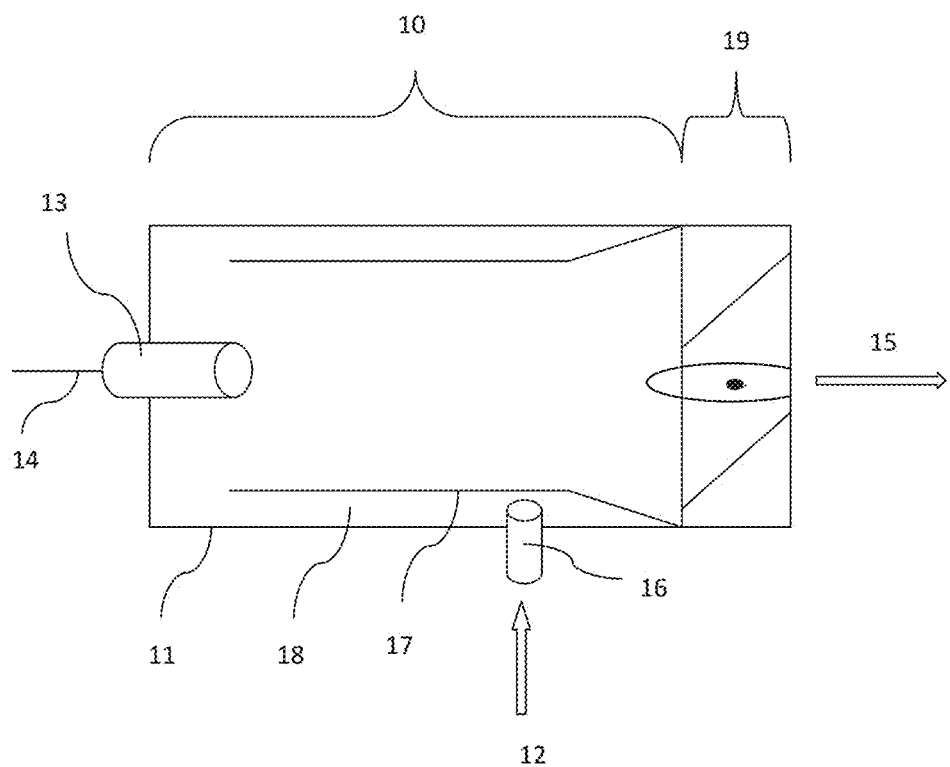
FIG. 1 is a schematic of a combustion-type heating chamber.

Disclosed herein is an improved thermal fogging unit. In general, thermal fogging units are capable of breaking up treatment chemicals into minute particles by a combination of heat and gas velocity (i.e., thermal and kinetic energy input). Some thermal foggers may couple the heating means with another method useful for dividing the liquid chemical stream into minute particles. For example, in addition to the heating means, some thermal foggers also include an atomizing nozzle to inject the liquid chemical stream into the aerosolization chamber. Cold fogging units, on the other hand, break treatment chemicals up by mechanical means rather than with heat, such as with the use of an atomizer. Cold foggers generally are not capable of forming fogs typically required for many large-scale industrial purposes such as large crop storage facilities. The size and uniformity of aerosol particles may differ based on whether they are created in a thermal fogger or a cold fogger.

A thermal fogger, as the term is used herein, refers to a device used to create aerosols by combining a hot stream of gas or a heat source (e.g., combustion gases, hot air, etc.) and a stream of liquid treatment chemical in an aerosolization chamber. The resulting aerosols are typically minute liquid droplets (often having a size of one to ten micrometers), which, depending upon the type of chemical aerosolized, may form solid minute particles or crystals upon cooling. By way of non-limiting example, CIPC aerosols form minute crystals after cooling. Other crop storage treatment chemicals such as 1,4 dimethyl naphthalene, volatile essential oils, aldehydes and alcohols, etc., initially vaporize and then condense into aerosol-size liquid droplets.

Thermal foggers create aerosols generally by a contribution of thermal energy and kinetic energy (e.g., pneumatic energy) imparted by the hot gas stream or heat source impacting the liquid chemical stream. For example, the temperature of a hot gas stream may be from between about 120° C. (approximately 250° F.) to about 425° C. (approximately 800° F.), although typical ranges are from about 235° C. (approximately 450° F.) to about 345° C. (approximately 650° F.).

In a particular embodiment, an aerosol is formed by contacting a liquid chemical stream with a hot gas stream. The liquid or molten chemical is aerosolized by the hot gas stream. A thermal fogger may include an elongated extended-surface area member which facilitates the mixing of the hot gas and liquid chemical in the aerosolization chamber. In one embodiment, the elongated mixing element of this invention is a spiral-shaped elongated member with a substantially continuous surface. In another embodiment, the elongated mixing element is sized and shaped to be retrofitted into various types of thermal foggers whether such devices comprise large or small aerosolization chambers and regardless of whether the hot gas stream is provided electrically or via combustion. An elongated mixing element may be adapted and configured to provide an advantageous increase in the surface area within the aerosolization chamber used to heat the aerosol mixture. Additionally, such an elongated mixing means may also provide turbulent flow, increased gas velocity, and increased mixing of the hot air stream with the liquid chemical to form a stable and uniform aerosol. Further, such a mixing means may provide an extended hot surface to improve transfer of thermal energy into the liquid chemical to facilitate formation of a stable aerosol.

In some embodiments, thermal foggers create a hot gas stream by combustion of a hydrocarbon based fuel, while other thermal fogging units create a hot air stream with electric heating means such as an electric strip heater, an electric heat exchanger, or electric heating coils or wires. The hot gas stream may thus include either hot combustion gases or hot air. The hot gas or hot air stream heats the liquid chemical and aids in aerosolization of the liquid chemical as it travels in a tortuous or circuitous path along the length of the extended-surface area member.

In one example of thermal fogging, a hot gas stream travels from a heating chamber to an aerosolization chamber where it is mixed with a liquid chemical stream to create an aerosol. The hot gas stream typically has a temperature between about 120° C. (approximately 250° F.) to about 425° C. (approximately 800° F.), although typical ranges are from about 235° C. (approximately 450° F.) to about 345° C. (approximately 650° F.), and more particularly, between about 315° C. (approximately 600° F.) and about 345° C. (approximately 650° F.).

Referring to FIG. 1, a typical combustion-type heating chamber 10 is shown. Such a combustion chamber is described in U.S. Pat. No. 6,322,002 to Forsythe et al., which is incorporated herein by reference in its entirety. FIG. 1 is a schematic sketch of a combustion-type thermal fogger having a heating chamber 10 and a stator (flame arrestor) 19.

The heating chamber 10 is formed by a barrel 11, generally having a cylindrical, large pipe, with an outer diameter between about 6 inches and 12 inches, although the diameter may be larger or smaller, depending on the particular application. The proximal end of the barrel 11 includes a port for insertion of a combustion burner 13 with an associated fuel line 14. Fuel line 14 carries fuels suitable for combustion, such as, for example, propane or natural gas. An inner cylindrical member 17 is substantially concentric with barrel 11 and is positioned inside the barrel 11. Air inlet pipe 16 introduces air stream 12 into annular space 18 formed between the inner cylindrical member 17 and the inner diameter shell of the barrel 11. Generally, the air inlet pipe 16 is close in proximity to the distal end or the downstream terminus of the heating chamber 10 so that the air introduced into the annular space 18 flows counter-current to the hot combustion gases and flame produced by combustion burner 13.

The inner cylindrical member 17 is flared to form a cone at its downstream section in the heating chamber 10 so that air introduced through air inlet pipe 16 must flow counter-currently to the hot combustion gases. The cone is sealed to the outer barrel 11 adjacent the terminus of the combustion zone heating chamber 10. It is at this point that a stator vane assembly 19 is positioned to act potentially as a flame arrestor and to cause the air and combustion gases to flow in a turbulent manner into the aerosolization chamber 20.

The stator vane assembly 19 may include any device that arrests the flame from the heating chamber 10 and prevents such flames from entering the aerosolization chamber. The stator vane assembly 19 is set at an angle to the combustion gas flow exiting the heating chamber 10 to provide efficient flame arresting characteristics in case of abnormal operation of the combustion burner 13 or the combustion zone heating chamber 10. This angular positioning causes the hot gases exiting the heating chamber 10 to flow in a turbulent manner into the aerosolization chamber 20. Such flame arrestors, however, as may be readily appreciated, are unnecessary in electrically heated thermofoggers.

While the above describes a particular embodiment of a thermofogger, the instant invention may be utilized in any suitable thermofogger, such as LECO™, XEDA™, DYNA FOG™ and similarly configured thermofoggers.

Figure 2:
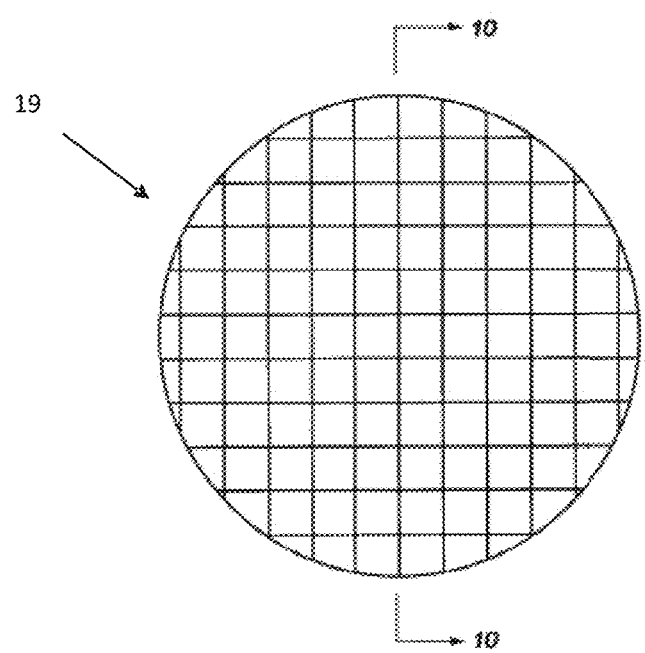
FIG. 2 is an elevational view of a grid-like stator assembly according to an embodiment.
Figure 3:
FIG. 3 is a cross-sectional view of the stator of FIG. 2.

FIG. 2 is an elevational view of an embodiment of a stator vane assembly 19 in which a grid-like assemblage of vanes are utilized to direct gases flowing therethrough into a turbulent pattern. FIG. 3 is a cross-sectional view along section lines 10-10 of FIG. 2. The vanes in the center form a V-shape directing the flow of gas outwardly. The vanes are positioned symmetrically about both the horizontal and vertical axes so that a sectional elevational view and a sectional plan view are visually the same. The gases flowing through this grid-like vaned stator must change direction and are directed generally outwardly to impact the outer barrel of the aerosolization chamber and rebound to create a turbulent flow in the heating chamber 10.

As an alternative to forming the hot gas stream 15 in a combustion-type heating chamber 10, the hot gas stream 15 may be formed by heating an air stream with one or more electric heating elements. Creating hot gas stream 15 by heating an air stream electrically may be advantageous to forming the hot gas stream 15 in a combustion chamber for several reasons, as described below. After heating and mixing with the liquid chemical stream 25, the heated gases exit the thermal fogger and enter a crop storage facility (e.g., potato storage facility). The heated gases in the hot gas stream 15 may increase the pressure within the crop storage facility. When the hot gas stream 15 is air, the pressure in the storage facility may not increase as dramatically as when the hot gas stream is derived by combustion of a hydrocarbon fuel, or may not even increase at all. Furthermore, combustion presents several safety hazards that are not present when the hot gas stream 15 includes only electrically heated air. Where a combustion chamber is used, the air from the storage facility cannot be recycled to the air inlet 16 without the potential of recycling some of the formed aerosol stream back into the combustion chamber. This may cause an explosion or fire hazard due to the flammability of the liquid chemical 15 dispersed in the aerosol. However, where the hot gas stream 15 is heated electrically, there is no such concern of explosion.

The hot gas stream 15 may be formed by an electric heating element capable of heating air to a temperature of between about 120° C. (approximately 250° F.) to about 425° C. (approximately 800° F.), although typical ranges are from about 235° C. (approximately 450° F.) to about 345° C. (approximately 650° F.). Any type of electric heating element is suitable, such as, for example, heating elements that use Joule Heating (also known as resistive heating), wherein the heat output is a function of the current applied to the electric heating elements and the resistance of the heating elements. For example, suitable electric heaters include electrical resistor heaters wherein a heating element is heated when an electric current encounters resistance in the heating element. The heating element may be a wire, a ribbon, or an electrical strip. The wire or ribbon may be straight, or it may be coiled within the heating chamber 10. By way of non-limiting example, electric heating elements may be lined around the heating chamber 10 or may be coiled within the heating chamber 10. A wire, ribbon, or electrical strip may be selected to have a desired electrical resistance and thus, capable of being heated to a given preselected temperature.

Where the electric heating element is a strip heater, the strip heater may be selected to heat air to a predetermined temperature. The strip heater may be a finned strip heater, ceramic insulated strip heater, or a plurality of ring heaters, such as are commercially available from Omega Engineering, Inc., of Stamford, Conn. The strip heater may be mounted in the heating chamber 10 wherein air is caused to pass through and over the strip heater. The heating chamber 10 may include a plurality of strip heaters to increase the overall heating efficiency of the heating chamber 10. By way of non-limiting example, the heating chamber 10 may include a series of ring heaters placed within the cylinder of the heating chamber 10. As another example, a plurality of ring heaters may be used in combination with other styles of strip heaters.

In another embodiment, the electric heating element may be an electric heat exchanger as disclosed and described in U.S. Pat. No. 5,935,660 to Forsythe el al. The electric heat exchanger may be capable of heating a large quantity of air to at least about 425° C. (approximately 800° F.), with typical outlet temperatures ranging between about 315° C. (approximately 600° F.) and about 345° C. (approximately 650° F.), or any desirable temperature, depending on the particular application of the thermal fogger.

Figure 4:
FIG. 4 is a schematic of a typical electric heating coil.
Figure 5:
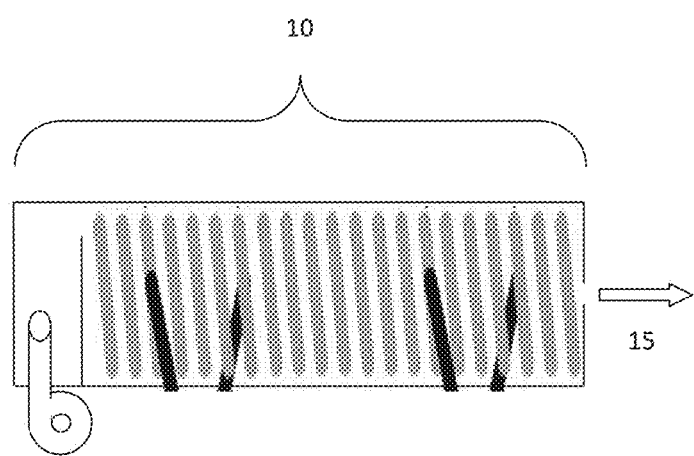
FIG. 5 is a schematic of a typical electric heating chamber where the heating means are electrical coils.

Other electric heating elements may include coil heaters, such as those available from NextThermal, of Battle Creek, Mich. The coil heater may be an electric heating element similar to that shown in FIG. 4, where a current carrying metal is coiled into a generally helical shape. The hot gas stream 15 may be heated by including several lengths of electric heating coils within the heating chamber 10, as illustrated in FIG. 5. For example, the heating chamber 10 may include a tube that is lined on the inside with several lengths of electric heating coils through which air must travel to exit the heating chamber 10 prior to entering the aerosolization chamber.

The electric heating elements described above may be selected to have a power rating that is approximately twice that typically required to heat a flow rate of about 10 cfm to about 50 cfm, a flow rate of about 50 cfm to about 150 cfm, or a flow rate of about 150 cfm to about 300 cfm, although the flow rate may be higher depending on the particular application of the thermal fogger and the particular storage facility. The airflow may be directly related to the heater size in watts and to the difference in temperature between the inlet and the outlet of the electric heater. The electric heating means may be configured and adapted to be compatible with various power sources, such as, for example, single or 3-phase electric power, connection with various power generators, various line voltages, and other types of power sources. For example, where the storage facility is in a remote location, the thermal fogger may be adapted to be powered by a power generator.

The temperature of the hot gas stream 15, whether heated electrically or from a combustion chamber, may be controlled by a simple feedback control loop. For example, a thermocouple may be located or mounted at the outlet of the heating chamber 10, or at the inlet of the aerosolization chamber. The thermocouple may be coupled to a temperature controller. If the setpoint of the temperature controller is higher than the temperature of the hot gas stream 15, the feedback controller sends a signal to increase the fuel in the combustion chamber or to increase the temperature (i.e., by increasing the current to the electric heater) of the electric heaters. If the temperature is higher than the setpoint, either combustion gas flow or electric current can be decreased until the temperature reaches the desired temperature. In one embodiment, a temperature probe is located at the exhaust of the heating chamber 10 to measure the temperature of the hot gas stream 15. An additional temperature probe may be located at the exhaust of the aerosolization chamber to measure the temperature of the aerosol. If the temperature of the aerosol exiting the aerosolization chamber is lower than desired, the liquid chemical flow rate may be decreased or the heater output may be increased. Thus, if the aerosol temperature is other than desired, the liquid chemical flow may be adjusted to achieve the desired temperature of the aerosol exiting the aerosolization chamber. An electric controller may control the temperature of the hot gas stream 15 entering the aerosolization chamber. The aerosol temperature may be controlled by either manually or automatically adjusting the chemical flow rate. For example, if the aerosol temperature is too low, the chemical flow rate may be decreased to increase the temperature of the aerosol exiting the aersolization chamber. Thus, in some embodiments, the aerosol outlet temperature may be controlled by adjusting the chemical flow rate and by maintaining the heat input into the thermal fogger. The target aerosol temperature may be selected based on the chemical storage conditions, ambient conditions, and other treatment needs.

Figure 6:
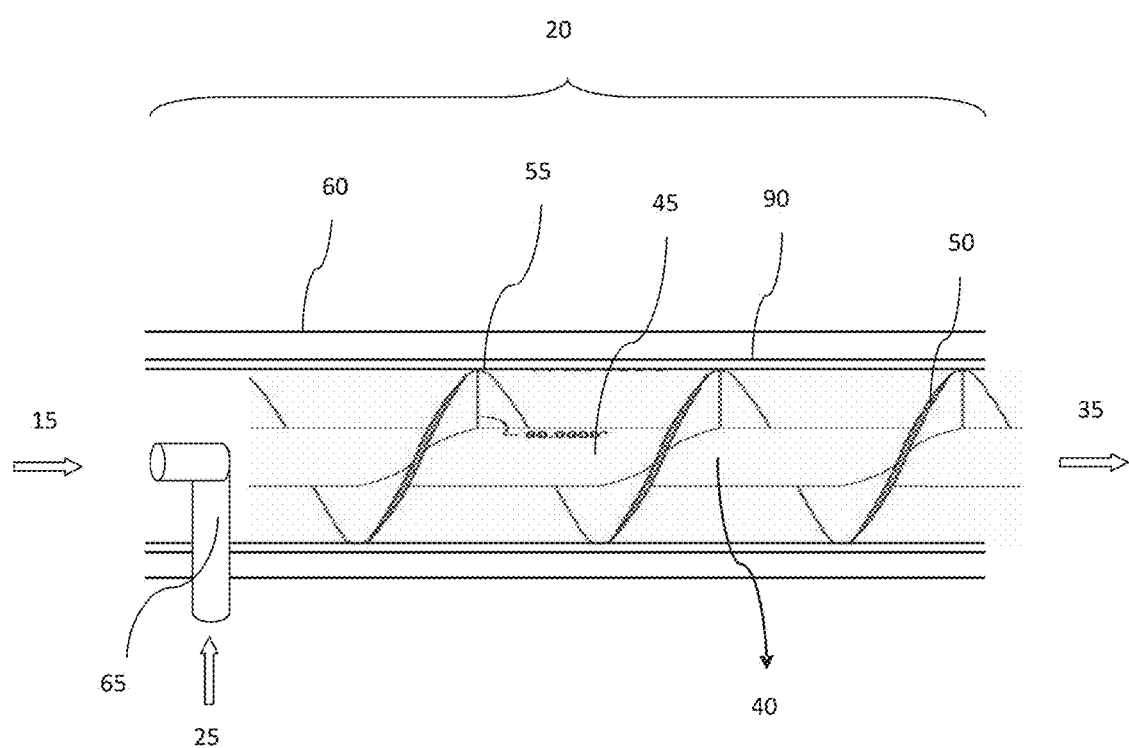
FIG. 6 is a schematic of an aerosol formation zone with a helically-shaped mixing means insert according to a particular embodiment.

Referring to FIG. 6, an embodiment of a thermal fogger aerosolization chamber 20 with mixing means 40 is shown. After the hot gas stream 15 is formed in the heating chamber 10, the hot gas stream 15 enters the aerosolization chamber 20. The hot gas stream 15 may be formed in any type of heating chamber 10. The embodiment of FIG. 6 includes a mixing means 40 with an inner solid central shaft 45 that are sealed within a sealed tube 55 outside the mixing means 40. The sealed tube 55 may then be inserted within the barrel 90 of the aerosolization chamber 20. In another embodiment, the mixing means can be inserted directly into the barrel 90 of the aerosolization chamber 20 without the sealed tube 55. The thermal fogger may include a layer of surrounding insulation 60 to increase the thermal efficiency of the thermal fogger.

The heating chamber 10 is in communication (i.e., in close proximity to or adjacent to) with the aerosolization chamber 20. The heating chamber 10 may be connected to the aerosolization chamber 20 by ducts, tubing, or a pipe that transfers hot gas stream 15 to the inlet of the aerosolization chamber 20. The aerosolization chamber 20 may be any chamber sufficient to provide adequate heat and mixing to form an aerosol from the hot got gas stream 15 and the liquid chemical stream 25. The aerosolization chamber 20 may include a liquid chemical introduction port 65 at or near the proximate end of the aerosolization chamber for introduction of the liquid chemical stream 25. As described in more detail below, the aerosolization chamber 20 may include an extended-surface element with a convoluted surface disposed longitudinally within the aerosolization chamber. At the outlet of the aerosolization chamber 20 is an outlet opening through which aerosol stream 35 exits the thermal fogger.

In the representative aerosolization chamber 20, the hot gas stream 15 contacts and mixes with the chemical stream 25. The liquid chemical stream 25 may be molten CIPC, CIPC in a solvent such as a lower alcohol (e.g., methanol), an essential oil such as clove oil, mint oil, 1/4 DMN, diisopropyl naphthalene and/or aldehydes, alcohols and the like described in U.S. Pat. No. 6,855,669 and U.S. Patent Publication 2009/0062126 to Knowles et al. or any other chemical to be aerosolized for chemical treatment in a produce storage facility. The desired temperature of the hot gas stream 15 is largely determined based on what chemical is selected for the liquid chemical stream 25.

The liquid chemical stream 25 may be injected into the aerosolization chamber either concurrently with the flow of the hot gas stream 15, or counter-currently to the hot gas stream 15. Thus, the liquid chemical stream 25 may enter the aerosolization chamber 20 facing the incoming hot gas stream 15, or facing the outlet of the aerosolization chamber 20. In many embodiments, the goal is to provide the optimum amount of mixing between the hot gas stream 15 and the liquid chemical 25. In one embodiment, the liquid chemical stream 25 may be dripped onto a hot plate, over which the hot gas stream 15 passes and carries vapors from the liquid chemical through the aerosolization chamber 20. In such an embodiment, the liquid chemical stream may be dripped onto an electrically heated hot plate or onto an otherwise heated plate to increase the efficiency of the vaporization of the liquid chemical. In another embodiment, the liquid chemical stream 25 is injected via a nozzle. The nozzle is such that liquid material is dispersed into droplets by the nozzle, which may increase the uniformity of the aerosol. In yet another embodiment, the liquid chemical stream 25 may be injected as a jet of liquid or stream of liquid material that strikes a dispersion or impingement plate to disperse the jet or stream of liquid material into droplets so that it forms an aerosol in the aerosolization chamber 20. The dispersion plate may also be electrically heated. In such an embodiment, the jet may be injected via a nozzle, such as, for example, an atomization nozzle.

Optimal aerosolization can be achieved by optimizing the contact time and the mixing between the liquid chemical stream 25 and the hot gas stream 15. Thus, it is generally desired to create and maintain turbulent flow of the liquid chemical stream 25 and the hot gas stream 15 in the aerosolization chamber 20. Mixing and heat transfer in the aerosolization chamber 20 can be enhanced by introducing a mixing means 40 into the chamber. The mixing means 40 causes the hot gas stream 15 and the liquid chemical stream 25 to travel a convoluted path and contact an extended-surface of hot metal before being discharged as an aerosol stream 35. The increased contact of the forming aerosol with the extended hot surface increases heat transfer to the forming aerosol. The mixing means 40 also increases the turbulent flow within the aerosolization chamber 20, thereby increasing the efficiency of aerosolization. The mixing means may include any number of shapes, such as for example, an elongated spiral-shaped member such as an auger or screw-shaped element or ribbon, a spiralled surface, disc or ring structures, or a number of baffles or flow-diversion blades that alter the flow path of the gases flowing through the aerosolization chamber 20. The mixing means 20 may have a longitudinal axial member that extends substantially the entire length of the elongated surface member, such as a screw-shaped element with a central shaft therethrough, e.g., spiral-shaped flights formed a continuous ribbon attached to an axial core member.

Figure 7:
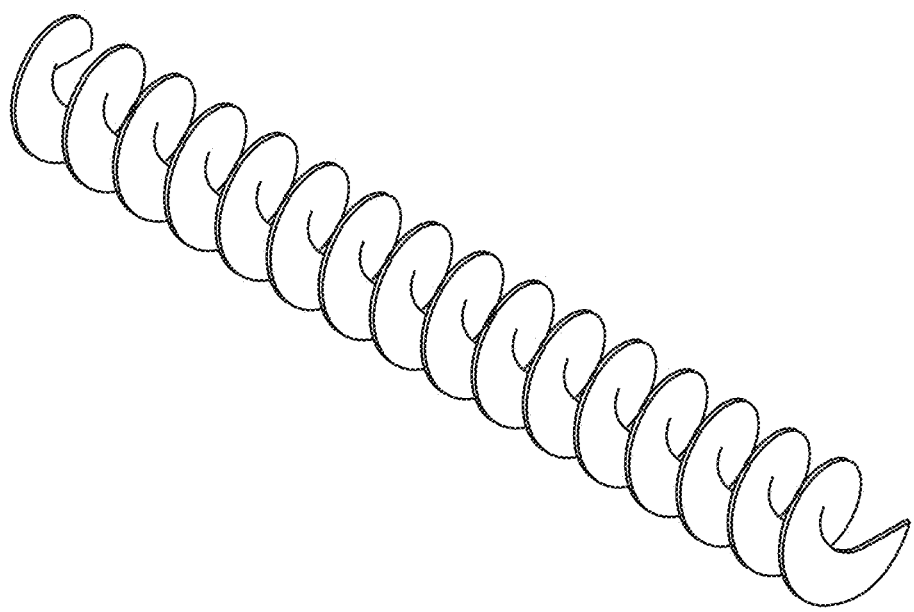
FIG. 7 is a schematic of one embodiment of a helically-shaped mixing means according to a particular embodiment.

In one embodiment, the mixing means 40 may be a helically-shaped insert that is similar to a screw conveyor or an auger, as shown in FIG. 6. The mixing means 40 may include a central shaft 45 and blades or flights 50 to cause a flow diversion through the aerosolization chamber 20. The central shaft 45 may be solid or may be a tubular structure. The blades 50 may be in the form of a continuous ribbon throughout the length of the aerosolization chamber 20. In another embodiment, the blades 50 may be formed of individual sections separately spaced throughout the length of the mixing means 40. In one embodiment, the mixing means 40 is built around a central shaft 45. Where the mixing means 40 includes a helically-shaped insert, the central shaft 45 may act as a type of heat sink to increase the total heat in the system, and to help maintain the high internal temperature on all sides of the helical path travelled by the nascent aerosol. In another embodiment, the mixing means 40 is not built around a central shaft 45, but rather, constitutes a helically-shaped elongated ribbon, as illustrated in FIG. 7. In this embodiment, the mixing means 40 is formed from a spiralled or helically-shaped piece of metal, but without a bore or shaft therethrough. Such a mixing means 40 may be advantageous in particular embodiments because it increases the total contact surface area within the aerosolization chamber 20 in the absence of a central shaft.

The hot gas stream 15 and the liquid chemical stream 25 mix as they flow through the aerosolization chamber 20. The two streams are brought into contact with the mixing means 40 which causes the hot gas stream 15 and the liquid chemical stream 25 to flow in a turbulent, circuitous, and convoluted path through the aerosolization chamber 20. In the absence of the mixing means 40, the hot gas stream 15 and the liquid chemical stream 25 may travel a substantially linear path directly through the aerosolization chamber 20. However, the mixing means 40 forces the liquid chemical and gas mixture against the walls or blades of the mixing means 40 to cause a constant change of direction. Thus, such a helically-shaped insert is particularly advantageous. The aerosol gases are forced to travel a convoluted path and contact much more hot metal surface than they would otherwise contact in the absence of the elongated-surface element of the mixing means 40.

The presence of the mixing means 40 within the aerosolization chamber 20 increases the effective length of the chamber. The extended-surface area of heat transfer surface on the mixing means 40 adds significantly to the inner surface area of a typical aerosolization chamber 20. As the mixing means 40 causes the forming aerosol to travel a circuitous path through the aerosolization chamber 20, the effective length of the aerosolization chamber 20 is thereby increased. Thus, effective thermal fogging devices may be created with a shorter chamber or barrel length than otherwise required because of the presence of the mixing means 40. In general, in the absence of the extended-surface element, the forming aerosol would only travel a distance of approximately the length of the aerosolization chamber 20 barrel. The mixing means 40, such as, for example, a helically-shaped insert, may increase the effective distance that the forming aerosol travels in the barrel by at least about 25% of the length of the aerosolization chamber 20, at least about 50% of the length, at least about 75% of the length, and at least by about 100% of the length of the aerosolization chamber 20.

The effective length of the aerosolization chamber 20 is a function of the path the forming aerosol has to travel as it passes through the aerosolization chamber 20. For example, where the mixing means is a helically-shaped insert such as a screw conveyor, changing the pitch of the blades or flights of the helically-shaped insert changes the effective length of the aerosol formation zone 20.

As described above, in addition to creating turbulent flow in the aerosolization chamber 20, the mixing means 40 can also increase the contact surface area of the metal within the aerosolization chamber 20, and therefore, increase the heat transfer between the hot metal surfaces and the forming aerosol mixture. The larger the surface area of the extended-surface element of the mixing means 40, the more heat transfer between the aerosol and the mixing means 40 in the aerosolization chamber 20. Specifically, the mixing means 40 can act to increase the effective length of the aerosolization chamber 20, which can increase the length of metal surfaces that the forming aerosol has to pass and come into direct contact with.

Figure 8A:
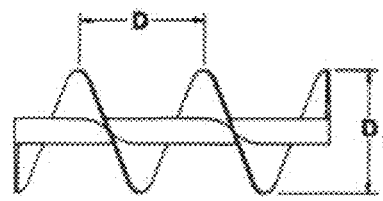
FIG. 8a through FIG. 8d are schematics of helically-shaped inserts with various pitches according to another embodiment.

The mixing means 40 may increase the effective length of the aerosolization chamber 20 by increasing the surface area that the forming aerosol gases must contact prior to exiting the aerosolization chamber 20. For a given length, where the mixing means 40 includes a helically-shaped insert, the effective surface area of the mixing means 40 may be altered by altering the pitch of the insert. The pitch generally refers to the distance between corresponding points on adjacent turns of the blades or flights of the auger or conveyor. Referring to FIG. 8a, in which a standard pitch conveyor is illustrated, the pitch is equal to dimension D, the outer diameter of the flights of the helically-shaped insert. In the standard pitch conveyor of FIG. 8a, D is the diameter of the conveyor and is also the pitch.

Figure 8B:
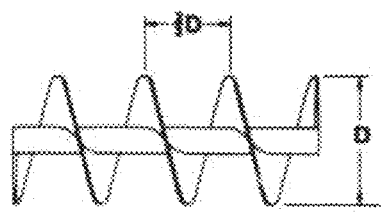
Figure 8C:
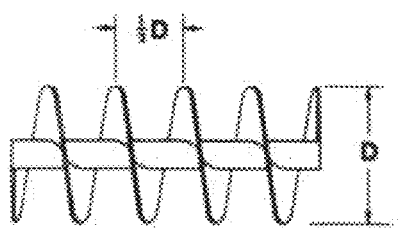
Figure 8D:
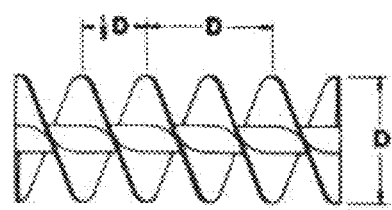

The shape and angular orientation of flights of the helically-shaped mixing means 40 may differ depending on the desired performance of the thermal fogger. For example, the helically-shaped mixing means 40 may be a standard pitch, single flight, wherein the pitch is equal to the diameter of the outermost portion of the helical device, as illustrated and described with respect to FIG. 8a. In another embodiment, the helically-shaped insert may be a short pitch, single flight device wherein the flight pitch is approximately ⅔ the diameter, as illustrated in FIG. 8b. Such a device may be used where improved thermal heat transfer is desired in the aerosolization chamber 20. For even more surface area, a device as illustrated in FIG. 8c may be used wherein the pitch is reduced to approximately ½ the diameter. Various other embodiments are contemplated, such as a double flight, standard pitch, as illustrated in FIG. 8d. The double flight, standard pitch embodiment includes a pair of spiral-shaped solid flights travelling the length of the mixing means 40. In yet other embodiments, the spiral-shaped mixing means 40, may include at least a pair of spiral-shaped flights. Thus, the helically-shaped insert may have flights with a pitch of between about ⅓ D to about ½ D, between about ½ D and about ⅔ D, between about ⅔ D and about D, between about D and about 1.5 D, or between about 1.5 D and about 2 D, where D is equal to the outside diameter of the helically-shaped insert.

As noted, the elongated surface element of the mixing means 40 may increase the total surface area the forming aerosol contacts within the aerosolization chamber 20. The total surface area within the aerosol formation zone may be increased by up to about 2 times the interior surface area of the barrel of the aerosol formation zone, up to about 5 times of such surface area, up to about 10 times of such surface area, and up to about 20 times of such surface area depending on the type of elongated surface element included with the mixing means 40.

Besides providing additional heat transfer surface, the mixing means described and illustrated herein provide impact surface whereby droplets of the injected liquid chemical collide with the blades, flights, etc., of said mixing means to fragment into smaller droplets thereby assisting in formation of a stable, desirable aerosol within or somewhat short aerosolization chamber.

Referring again to FIG. 6, in some embodiments, the mixing means 40 can be generally cylindrical and substantially concentric within the barrel of the aerosolization chamber 20. In such embodiments, the sealed tube 55 has an inner diameter that is substantially the same or slightly larger than the largest dimension of the mixing means 40 (such as, for example, the outer diameter of the mixing means 40). The mixing means 40 is sealed to the inside diameter of sealed tube 55 of the aerosolization chamber 20. Sealing the mixing means 40 to the inside diameter of sealed tube 55 disposed within the aerosolization chamber 20 prevents the hot gas stream 15 and the liquid chemical stream 25 from bypassing the mixing means 40 and travelling along the inner wall of the aerosolization chamber 20. This causes the two streams to more effectively mix as they pass through the aerosolization chamber 20. In one embodiment, where the mixing means 40 is a helically-shaped insert, the insert can be welded around the circumference of the inside diameter of sealed tube 55 at the distal end of the aerosolization chamber 20, thereby forcing the formed aerosol to exit the helically-shaped insert through the blades 50. The mixing means 40 may be sealed to the inside diameter of the sealed tube 55 by other methods, such as with a seal type material that can withstand the elevated temperatures within the aerosolization chamber 20. For example, in one embodiment, the mixing means 40 may include a seal on the outer diameter of the mixing means 40 to seal the mixing means 40 with either the inner diameter of the sealed tube 55 or the inner diameter of the barrel 90. In another embodiment, the mixing means may be shrink fitted (freeze fitted) into the sealed tube 55. The sealed tube 55 may be heated to temporarily increase the inside diameter of the sealed tube 55 and/or the mixing means 40 may be subjected to very cold temperatures to shrink the mixing means 40. The mixing means is placed into the sealed tube 55 when the mixing means 40 is at a substantially low temperature, when sealed tube 55 is at a substantially increased temperature, or when both the mixing means 40 is at a substantially low temperature and the sealed tube 55 is a substantially increased temperature. As the sealed tube 55 cools and the mixing means 40 returns to room temperature, the mixing means 40 is sealed within the sealed tube 55.

The mixing means is generally structured and adapted to increase significantly the velocity of the gases flowing through the aerosolization chamber 20 up to about 2 to 3 times the inlet velocity. In some embodiments, the increase in velocity may be up to about 4 to 8 times the inlet velocity. In one embodiment, the inner diameter of the barrel 90 and the outer diameter of the sealed tube 55 or mixing means 40 are substantially similar. As the forming aerosol enters the mixing means 40, the presence of the mixing means 40 reduced the cross-sectional opening area through which the aerosol may travel. The reduction in open cross-sectional area causes the velocity through the aerosolization chamber 20 to increase and promotes mixing within the chamber.

Advantageously, the mixing means 40 of the present invention may be useful in retrofitting already existing thermal foggers. Thus, the mixing means 40 may be an extended-surface element adapted and configured to fit within the aerosolization chamber 20 of an existing thermal fogger, such as a LECO™ or SUSPENSE™ thermofogger. The mixing means 40 may include an extended-surface to interrupt the otherwise linear flow of the forming aerosol material within the aerosolization chamber 20. The mixing means 40 causes the forming aerosol to travel a circuitous path before exiting the aerosolization chamber 20.

Figure 9:
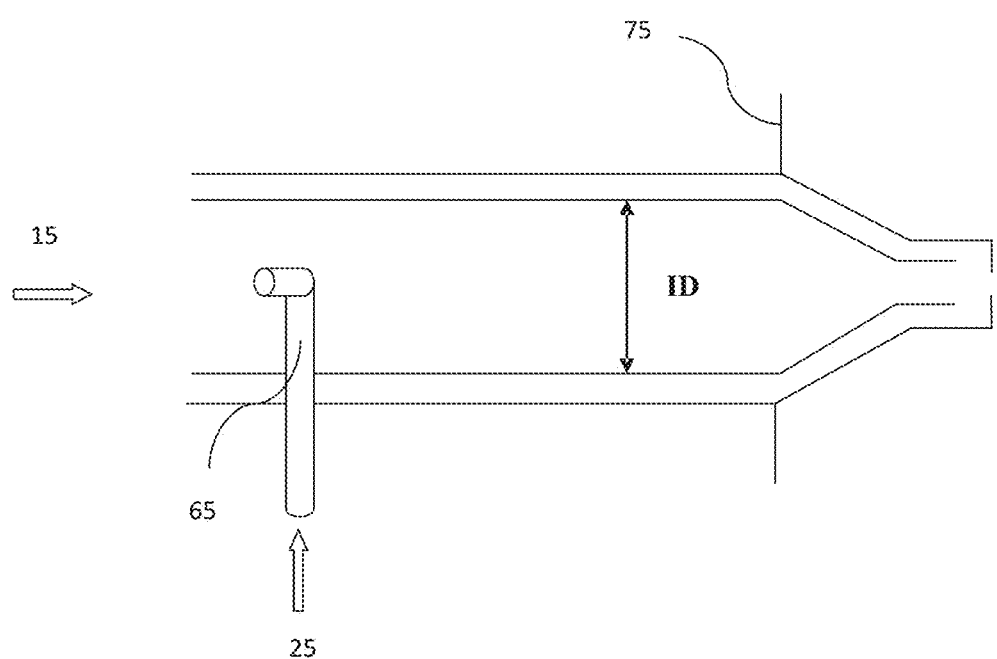
FIG. 9 is a schematic diagram of an existing thermal fogger unit to be retrofitted with a mixing means.

In the embodiment shown in FIG. 9, the liquid chemical stream 25 enters the thermal fogger via the liquid chemical introduction port 65. A mixing means 40 may be introduced into the thermal fogger where the mixing means 40 includes an extended-surface element, such as a helically-shaped insert. The helically-shaped insert may be placed into the existing thermal fogging unit proximate the liquid chemical introduction port 65. The aerosolization chamber 20 of the existing thermal fogger may be accessed by removing the nozzle end of the thermal fogger by unbolting flange 75. Once the nozzle end of the thermal fogger is removed from the main body of the fogger, the mixing means 40 may be placed into the aerosolization chamber of the exiting thermal fogger.

Figure 10:
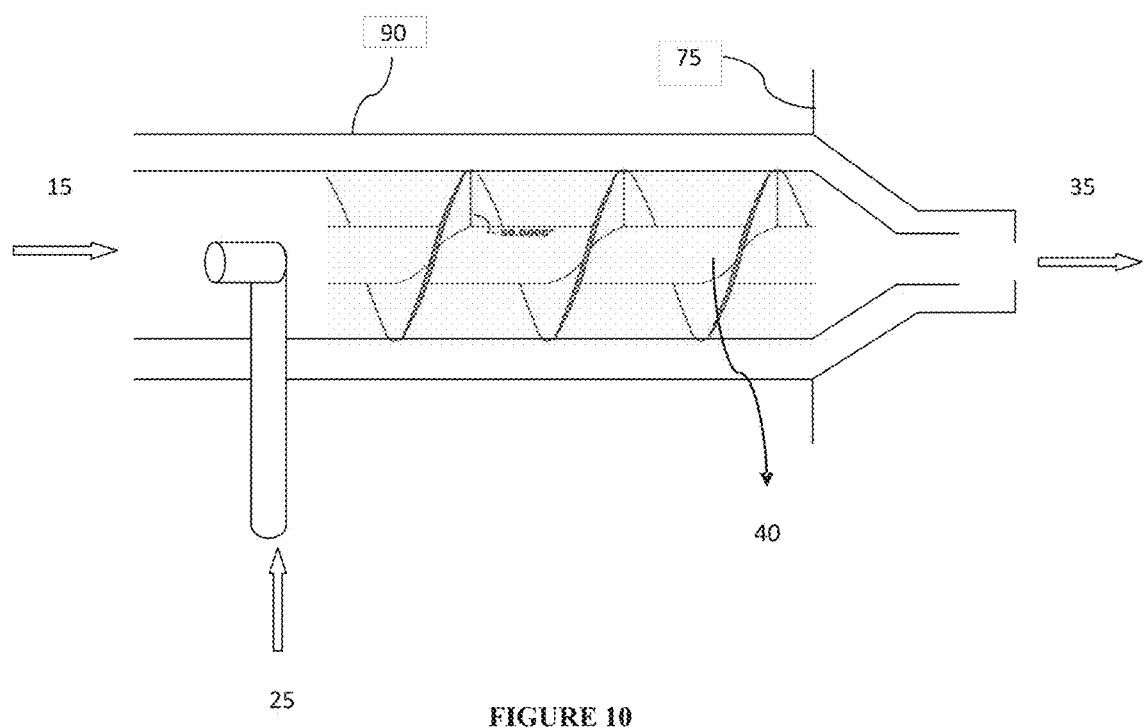
FIG. 10 is a retrofitted thermal fogger with a mixing means insert placed therein according to a particular embodiment.

The retrofit insert may have a length that is substantially the same as the length of the aerosolization barrel or aerosolization chamber 20 of the existing thermal fogger. Such a configuration with the retrofit mixing means 40 is shown in FIG. 10. For example, a typical thermal fogger will have an existing barrel 90 through which the aerosol is formed. The existing thermal fogger may have an existing inner diameter, ID, as shown in FIG. 9. The mixing means 40 may be designed with an outer diameter very close to the inner diameter of the existing thermal fogger to prevent the forming aerosol from bypassing along the outside of the mixing means 40 thereby causing proper and thorough mixing. The mixing means 40 insert can be selected to have an outside diameter very close to the inside diameter of the existing thermal fogging unit to ensure a tight fit and seal. Once the mixing means 40 is set in place, the ends of the unit may be tack welded at each end. In addition, the distal end may be circumferentially welded into place to ensure that the exiting vapors do not bypass the mixing means 40. In another embodiment, the mixing means 40 insert may be shrink fitted into place as described above. The thermal fogger may or may not be insulated, although it is generally preferred that the unit is insulated to preserve high heat transfer efficiency and minimize heat losses to the surrounding atmosphere.

Figure 11:
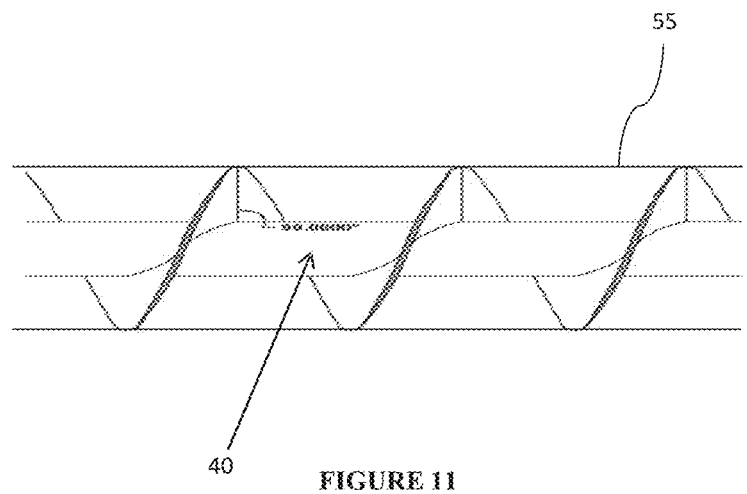
FIG. 11 is a schematic of an embodiment where the mixing means is sealed to a tube, which may then be placed into an aerosolization chamber according to another embodiment.
Figure 12:
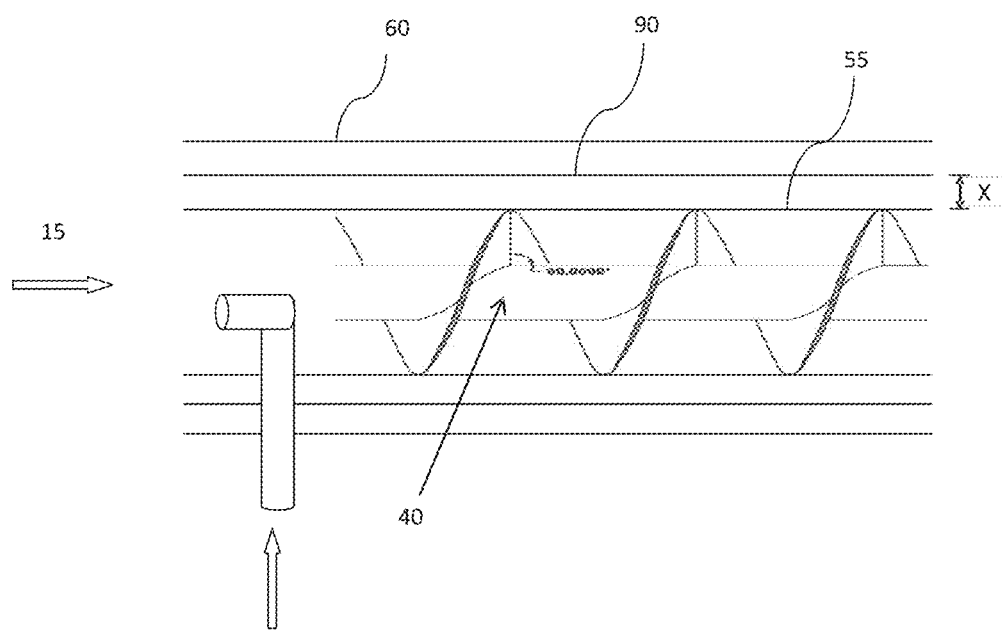
FIG. 12 is a thermal fogger including the insert of FIG. 11 where the mixing means is sealed within a tube prior to insertion into an aerosolization chamber according to a particular embodiment.

The retrofit mixing means 40 may include any number of shapes, such as for example, an elongated spiral-shaped member, a number of discs or rings arranged along the length of the aerosolization chamber, or a number of baffles or flow-diversion blades to alter the flow path of the gases flowing through the aerosolization chamber 20. In one embodiment, the retrofit mixing means 40 may be sealed to a tube (open cylinder) prior to insertion into the existing thermal fogger. Such an insert is shown in FIG. 11 wherein the mixing means 40 is sealed to a sealed tube 55 prior to inserting the mixing means 40 into the aerosolization chamber. Referring to FIG. 12, the sealed tube 55 with mixing means 40 is inserted into an existing thermal fogger. The sealed tube 55 has an outer diameter that is very close to the inner diameter of the barrel 90 of the existing thermal fogger. For example, distance X, shown in FIG. 12, may be very small such that the sealed tube 55 fits tightly within the diameter of the barrel 90 of the existing thermal fogger. The thermal fogger of FIG. 12 may optionally include a surrounding layer of insulation 60.

Advantageously, whether the mixing means 40 is placed in a new thermal fogger or in a retrofit thermal fogger, the mixing means 40 may be heated electrically. This may be especially advantageous in units where the hot gas stream 15 is produced by electrically heated air rather than via combustion, however, the mixing means 40 may still be electrically heated when hot gas stream 15 is formed from combustion. Heating the mixing means 40 provides extra heat to the thermal fogger and increases the heat transfer from the thermal fogger to the aerosol. The temperature to which the mixing means 40 is heated should generally not exceed the temperature of the hot gas entering the aerosolization chamber.

Figure 13:
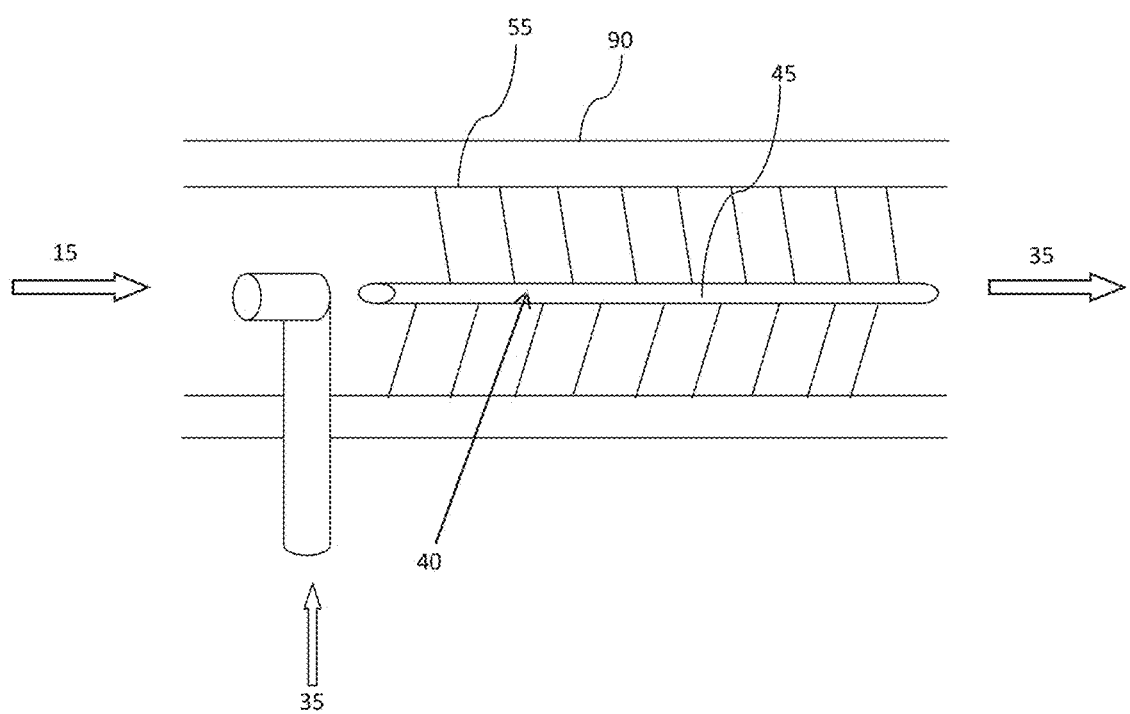
FIG. 13 is a schematic of an aerosolization chamber where the mixing means insert has baffles attached to a central core according to yet another embodiment.

Although the elongated surface element has generally been described as a mixing means 40, the elongated surface element may be any member that can be inserted into the barrel 90 of an aerosol formation zone to increase the heat transfer and impact surface area of the aerosol formation chamber 20. Such an elongated surface element may also increase turbulence within the chamber. In one embodiment, the elongated surface element may include a plurality of baffles throughout the barrel of the aerosolization chamber 20 as depicted in FIG. 13. Each of the baffles may be attached to a central shaft 45. The largest dimension (i.e., the distance from the end of one baffle to the end of another baffle) may be only slightly smaller than the inner diameter of the sealed tube 55. The baffles may be arranged in any manner such that the forming aerosol has to travel a tortuous path as it travels along the length of the aerosol formation chamber 20. It is noted that in these alternative embodiments, the elongated surface element may be electrically heated as described above.

The gases flowing through the aerosolization chamber 20, including the elongated surface element, travel an increased effective distance as they travel through the aerosolization barrel. The gases are caused to travel an elongated path where they encounter substantially more hot metal heat transfer surface area than they would otherwise encounter in the absence of the elongated surface element. The elongated surface element may also cause or increase the turbulence of the forming aerosols, thereby increasing the effectiveness of heat transfer within the aerosolization chamber 20.

Figure 14:
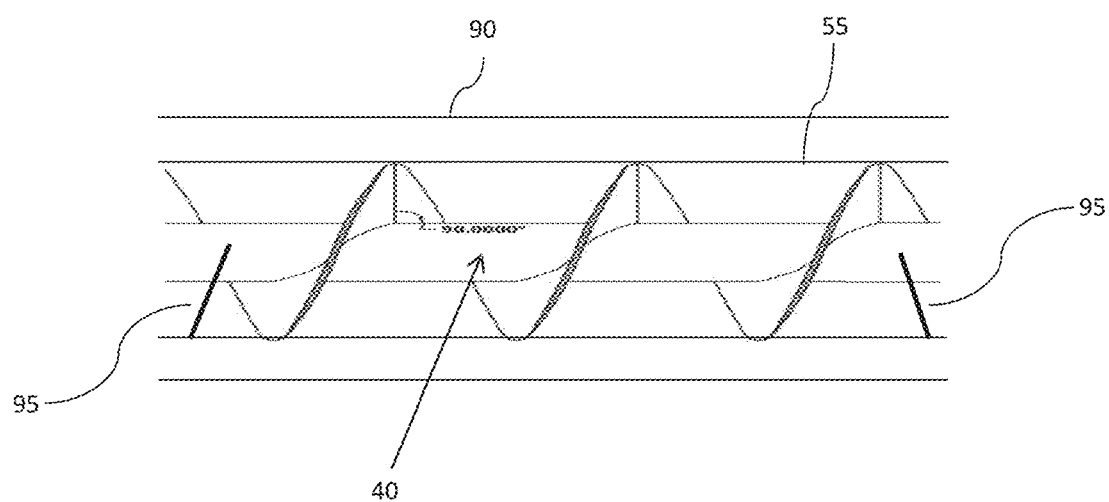
FIG. 14 is a schematic of a mixing means heated with electrical leads wherein the mixing means is disposed within a ceramic sealed tube according to a particular embodiment.

In yet another embodiment, as shown in FIG. 14, electrical leads 95 are connected to the mixing means 40. The electrical current flowing through the mixing means 40 and the electrical resistance of the mixing means 40 heats the mixing means 40. In another embodiment, the sealed tube 55 of FIG. 14 may include a ceramic tube or a tube coated with ceramic. The ceramic sealed tube 55 may be substantially resistant to heat and may also be substantially electrically insulated and thus provide protection when the electrical leads 95 are connected to the mixing means 40. Such an embodiment is advantageous because the electrical leads 95 via the electrical resistance of the metal mixing means causes the mixing means 40 to become hot while the ceramic sealed tube 55 electrically isolates the electrical leads 95 and the mixing means 40 from the barrel 90 of the thermal fogger.

Although the foregoing description contains many specifics, these are not to be construed as limiting the scope of the present invention, but merely as providing certain embodiments. Similarly, other embodiments of the invention may be devised which do not depart from the scope of the present invention. For example, features described herein with reference to one embodiment also may be provided in others of the embodiments described herein. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

The invention illustrated and described herein is useful particularly in improving the efficiency of electrically heated thermofoggers, especially those having sufficient capacity to be used for industrial purposes such as treating a crop storage facility with a crop-preserving chemical in an aerosol form within a period of a few hours. Potato storages are regularly treated with aerosols of sprout inhibitor chemicals, for example.

An example of an electrically heated thermofogger for such an industrial purpose is one operating from a voltage source of 220 to 240 volts with the capacity to heat a volumetric airflow of about 10 cfm to about 100 cfm to a temperature of about 200° C. (about 400° F.) to as high as about 400° C. (about 750° F.) to create a stable fog of a liquid chemical, such as 1,4 DMN introduced into the aerosolization chamber at a flow rate of about a few pounds per hour to about 100 lbs./hour or even more.

The electrical supply for such a thermofogger is generally at 220/240 volts and is typically three phase.

As described hereinabove, the mixing means insert in the aerosolization chamber facilitates the combination of thermal energy, kenetic (mechanical) energy of the hot flowing airstream to fragment liquid chemical droplets into minute particles (one to 10 microns, generally) to form a stable aerosol.

The spiral surface of certain inserts provides additional hot surface within the aerosolization chamber as well as additional impact surface to fragment the inspected liquid chemical droplets. Further, the various inserts described herein cause the flowing air stream/liquid chemical mixture to flow an extended convoluted path, thereby providing additional time for aerosol formation and creating turbulent flow which increases heat transfer efficiency between the hot surface of the insert, the surface walls of the aerosolization chamber and the hot air/liquid chemical mixture.

EXAMPLE

Electrically heated thermofoggers of various wattages and configurations are able to handle a variety of liquid chemicals with a wide range of flow rates.

| Thermofoggers | Insert | Capacity |
|---|---|---|
| #1 | 6 KW ~/in OD length ~18# inches Flight Pitch ~0.75 of OD | 6-8 liters/hr of 1,4 DMN |
| #2 | 16 KW ~2 inches OD length ~21 inches Flight Pitch ~1.0 of OD | 40-60 lbs./hr of molten CIPC |
| #3 | 40 KW ~3 inches OD length ~24 inches Flight Pitch ~1.0 of OD | 100 lbs./hr of molten CIPC |

Each of the above-identified thermofoggers produces a hot air stream at temperatures varying from about 400° F. to about 800° F. at sufficiently high volumetric flow rates to provide stable aerosols of the liquid chemicals identified above at those flow rates.

The above-identified capacities are those which have been tested with each of these thermofoggers having capabilities to handle both lower and higher flow rates of liquid chemicals.

The smaller #1 thermofogger operated over a 6 hour period has the capability to provide up to at least 48 liters of 1,4 DMN to a potato storage facility. Typically, effective sprout inhibition is attained at a residue level of about 2 ppm for 1,4 DMN. Thus, 48 liters, approximately 100 lbs., can provide sprout inhibition to a potato storage containing upwards of 50 million pounds of potatoes, assuming 100% efficiency of residue deposit. Even at an efficiency of 50%, a storage of 25 million pounds could be effectively treated.

The two larger thermofoggers were tested with molten CIPC, which has been a standard in the potato storage industry for over 15 years. The #3 thermofogger with a nominal capacity of 100 lbs./hr of CIPC could, over a six hour period, treat successfully a potato storage unit having up to about 100 million pounds of potatoes at a residue of 6 ppm at an efficiency of 100%, or upwards of 50 million pounds at an efficiency of 50%. A residue level of 6 ppm is sufficient to preclude sprouting of potatoes for many months.

In treating crops with an aerosol of 1,4 DMN, which has a boiling point of about 268° C. (~514° F.), it is desirable to have a hot air source at a temperature of from about 450° F. to about 550° F. while for treatment with CIPC, molten or in solution in methanol or similar solvent, a hot air source at a temperature of about 500° F. to about 650° F. or higher is desirable. Each of the thermofoggers described herein, have such capabilities.

The above-cited devices may be altered or modified in accordance with the precepts of this invention to have smaller or greater capabilities. The inclusion of the type of inserts illustrated and described herein to create an extended hot surface of additional impact area and the creation of convoluted, increased flow length enhances the aerosolization ability of electrically heated or combustion type thermofoggers.

Figure 15:
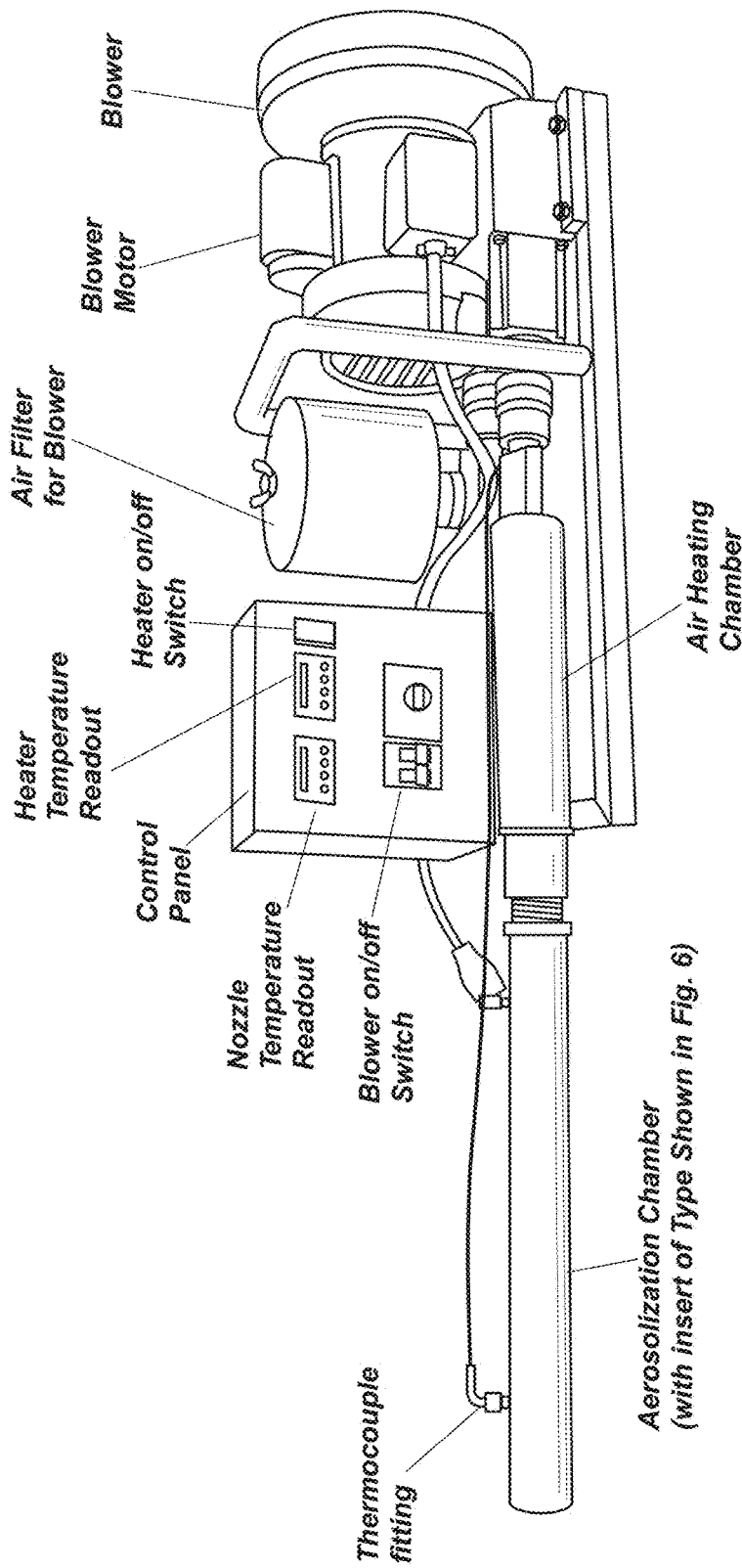
FIG. 15 is an illustration of an overall view of an electrically heated thermofogger according to an embodiment.

The electrically heated thermofogger illustrated in FIG. 15 employed an insert of the type shown in FIG. 6 to provide a high capacity of stable aerosols from liquid chemicals introduced into the proximal end of the aerosolization chamber. The tests described in the Example set forth hereinabove were performed with thermofoggers of this general type and structure. The size and weight of this illustrated fogger is such that it can be handled by an operator, placed upon an appropriate support structure and have the terminal end of the fogger placed through a wall of a crop storage facility. Alternatively, one or more of such thermofoggers can be mounted on or in a pickup truck bed or trailer to provide aerosol through a flexible conduit to a crop storage facility.

If desired, headspace air from a crop storage facility may be directed to the inlet of the thermofogger's blower to diminish or eliminate any overpressure caused by introduction of the aerosolized chemical into such a facility.

What is claimed is:

1. A thermal fogger for creating stable aerosols from a liquid material, comprising:
   a heating chamber; and
   an elongated aerosolization chamber in communication with the heating chamber, the elongated aerosolization chamber comprising:
      an introduction port defined in a proximal end of the elongated aerosolization chamber;
      an extended-surface element disposed longitudinally within the elongated aerosolization chamber, the extended-surface element comprising a convoluted surface; and
      an outlet opening defined at a distal end of the elongated aerosolization chamber,
   wherein the extended-surface element further comprises:
      flow diversion blades defining the convoluted surface, the flow diversion blades having a substantially uniform maximum diameter about equal to an inner diameter of the elongated aerosolization chamber.

2. The thermal fogger of claim 1, wherein the heating chamber comprises heating means to heat a flow of gas to a predetermined temperature.

3. The thermal fogger of claim 2, wherein the heating means comprises at least one of a combustion-type heater or an electric heater.

4. The thermal fogger of claim 2, wherein the heating means comprises at least one electric heating means.

5. The thermal fogger of claim 4, wherein the at least one electric heating means comprises at least one of an electric heating coil, an electric strip heater or additional electrical leads.

6. The thermal fogger of claim 1, wherein the extended-surface element has a length substantially coterminous with the elongated aerosolization chamber.

7. The thermal fogger of claim 1, wherein the flow diversion blades are attached to a central longitudinal core of the extended-surface element, the flow diversion blades defining a substantially continuous helically-shaped ribbon.

8. The thermal fogger of claim 7, wherein the flow diversion blades are shaped to define a flow path that is at least 50% greater than the length of the elongated aerosolization chamber.

9. A method for operating the thermal fogger of claim 1 to form a stable aerosol from a liquid introduced into a hot gas stream comprising:
   in the heating chamber of the thermal fogger, heating a gas to a foredeteremined elevated temperature;
   flowing the gas into the elongated aerosolization chamber;
   introducing through the introduction port, a liquid to create a gas-liquid mixture in the elongated aerosolization chamber;
   flowing the gas-liquid mixture along a convoluted path defined by the convoluted surface of the elongated aerosolization chamber to form a stable aerosol; and
   discharging the stable aerosol from the elongated aerosolization chamber through the outlet.

10. A thermal fogger for creating stable aerosols from a liquid material, comprising:
   a heating chamber; and
   an elongated aerosolization chamber in communication with the heating chamber, the elongated aerosolization chamber comprising:
      an introduction port defined in a proximal end of the elongated aerosolization chamber;
      an extended-surface element disposed longitudinally within the elongated aerosolization chamber, the extended-surface element comprising a convoluted surface; and
      an outlet opening defined at a distal end of the elongated aerosolization chamber,
   wherein the extended-surface element is configured as a screw-shaped element comprising at least a pair of the spiral-shaped and substantially solid flights extending substantially the entire length of the screw-shaped element, the flights having a substantially uniform maximum diameter substantially equal to an inside diameter of the elongated aerosolization chamber, the elongated aerosolization chamber being tubular shaped, the extended-surface element having a length substantially equal to the length of the elongated aerosolization chamber.

11. The thermal fogger of claim 10, wherein the flights have a pitch of about one half the substantially uniform maximum diameter of the screw-shaped element to about two times the substantially uniform maximum diameter of the screw-shaped element.

12. The thermal fogger of claim 10, wherein the flights comprise a continuous ribbon.

13. The thermal fogger of claim 10, wherein the flights comprise one or more baffles.

14. The thermal fogger of claim 10, wherein the surface area of the screw-shaped element is about one half times to about two times of the interior surface area of the elongated aerosolization chamber.

* * * * *